United States Patent [19]

Kuslich et al.

[11] Patent Number: 5,062,845
[45] Date of Patent: Nov. 5, 1991

[54] METHOD OF MAKING AN INTERVERTEBRAL REAMER

[75] Inventors: Stephen D. Kuslich, Maplewood; James D. Corin, Minneapolis, both of Minn.

[73] Assignee: Spine-Tech, Inc., Minneapolis, Minn.

[21] Appl. No.: 350,050

[22] Filed: May 10, 1989

[51] Int. Cl.$^5$ ............................................. A61B 17/56
[52] U.S. Cl. ..................................... 606/80; 606/182; 408/178
[58] Field of Search ............................... 606/180–183, 606/79, 80; 623/22, 23; 408/178, 173–177, 157

[56] References Cited

U.S. PATENT DOCUMENTS

| | | | |
|---|---|---|---|
| 16,151 | 12/1856 | Cole | 408/178 |
| 376,427 | 1/1888 | Cassidy | 408/175 |
| 817,042 | 4/1906 | Burns | 408/178 |
| 1,079,630 | 11/1913 | Baum | 408/175 |
| 1,409,825 | 3/1922 | Brush | 408/175 |
| 2,677,369 | 5/1954 | Knowies | 606/61 |
| 3,426,364 | 2/1969 | Lamb | 623/17 |
| 3,554,192 | 1/1971 | Isberner | 606/80 |
| 3,630,204 | 12/1971 | Fishbein | 606/81 |
| 3,633,583 | 1/1972 | Fishbein | 606/81 |
| 3,702,611 | 11/1972 | Fishbein | 606/81 |
| 3,875,595 | 4/1975 | Froning | 623/17 |
| 4,011,602 | 3/1977 | Rybicki et al. | 623/16 |
| 4,013,071 | 3/1977 | Rosenberg | 606/73 |
| 4,044,508 | 8/1977 | Frederick | 408/157 X |
| 4,059,115 | 11/1977 | Jumashev | 606/82 |
| 4,140,432 | 2/1979 | Heule | 408/157 X |
| 4,162,867 | 7/1979 | Calcaterra et al. | 408/157 |
| 4,309,777 | 1/1982 | Patil | 623/17 |
| 4,349,921 | 9/1982 | Kuntz | 623/17 |
| 4,369,769 | 1/1983 | Edwards | 606/61 |
| 4,401,112 | 8/1983 | Rezaian | 606/61 |
| 4,447,915 | 5/1984 | Weber | 606/95 |
| 4,468,200 | 8/1984 | Munch | 433/174 |
| 4,473,070 | 9/1984 | Matthews et al. | 606/80 |

(List continued on next page.)

FOREIGN PATENT DOCUMENTS 2931508 2/1981 Fed. Rep. of Germany ...... 408/176

OTHER PUBLICATIONS

Lesions of the Intervertebral Disks and their Treatment by Interbody Fusion Methods by Ralph Cloward.
Vol. 61-A, No. 8, Journal of Bone and Joint Surgery, Anterior Fusion of the Lumbar Spine (Dec. 1979).
No. 179, Clinical Orthopedics, Posterior Intervertebral Body Fusion (Oct. 1983).
Vol. 6, No. 3 Permanente Foundation Medical Bulletin, The Removal of Lower Lumbar Intervertebral Discs by the Transabdominal Extraperitoneal Route (Jul. 1948).
Vol. 50-A, No. 1, Journal of Bone and Joint Surgery, Methods of Lumbar Fusion (Jan. 1968).
Surgery, Gynecology and Obstetrics, Intercorporal Bone Graft in Spinal Fusion after Disc Removal.
Vol. 1, No. 2, Neurosurgery, A Technical Modification of Cloward's Posterior Lumbar Interbody Fusion (1977).
Clinical Orthopedic, No. 35 Intervertebral Body Fusion by the Use of Posterior Bone Dowel.

*Primary Examiner*—Robert A. Hafer
*Assistant Examiner*—Kevin G. Rooney
*Attorney, Agent, or Firm*—Merchant, Gould, Smith, Edell, Welter & Schmidt

[57] ABSTRACT

A surgical tool is disclosed for use in spinal stabilization for fusing contiguous vertebra in an animal spine. The tool includes a distal end having external dimensions sized for the distal end to be inserted within the animal body and located against a tissue layer between contiguous vertebra. Cutting blades are carried on the distal end for cutting at least a portion of the layer and at least a portion of vertebra bodies to form a chamber within the contiguous vertebra. The cutting blades are selected for the chamber to be sized greater than the external dimensions of the distal end. A control element is provided for controlling a depth of cut of the cutting blade between at least first and second positions with the cutting blade retained within the external dimensions when in the first position and with the cutting blade extended to form the chamber when in the second position.

12 Claims, 8 Drawing Sheets

U.S. PATENT DOCUMENTS

| | | | |
|---|---|---|---|
| 4,479,491 | 10/1984 | Martin | 606/61 |
| 4,501,269 | 2/1985 | Bagby | 606/61 |
| 4,545,374 | 10/1985 | Jacobson | 606/61 |
| 4,553,273 | 11/1985 | Wu | 623/18 |
| 4,554,914 | 11/1985 | Kapp et al. | 606/61 |
| 4,573,448 | 3/1986 | Kambin | 606/170 |
| 4,586,497 | 5/1986 | Dapra et al. | 606/80 |
| 4,589,414 | 5/1986 | Yoshida et al. | 606/79 X |
| 4,596,243 | 6/1986 | Bray | 606/80 |
| 4,599,086 | 7/1986 | Doty | 623/17 |
| 4,603,694 | 8/1986 | Wheeler | 606/79 X |
| 4,612,922 | 9/1986 | Barber | 606/80 X |
| 4,636,217 | 1/1987 | Ogilvie et al. | 623/17 |
| 4,644,951 | 2/1987 | Bays | 606/79 X |
| 4,646,738 | 3/1987 | Trott | 606/180 X |
| 4,653,481 | 3/1987 | Howland et al. | 128/69 |
| 4,657,550 | 4/1987 | Daher | 623/17 |
| 4,686,997 | 8/1987 | Oloff et al. | 606/180 X |
| 4,690,595 | 9/1987 | Heule | 408/173 X |
| 4,696,292 | 9/1987 | Heiple | 606/79 |
| 4,714,469 | 12/1987 | Kumma | 623/17 |
| 4,714,478 | 12/1987 | Fischer | 623/23 |
| 4,743,256 | 5/1988 | Brantigan | 623/17 |
| 4,756,649 | 7/1988 | Heule | 408/157 X |
| 4,772,287 | 9/1988 | Ray | 623/17 |
| 4,782,833 | 11/1988 | Einhorn et al. | 606/80 |

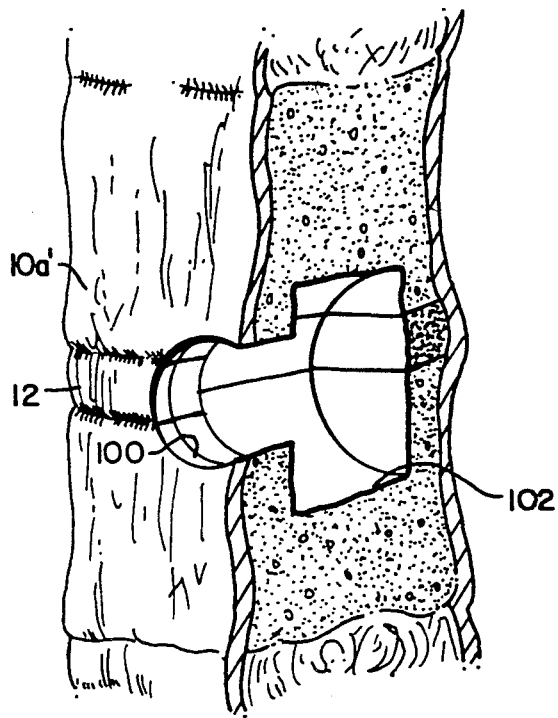
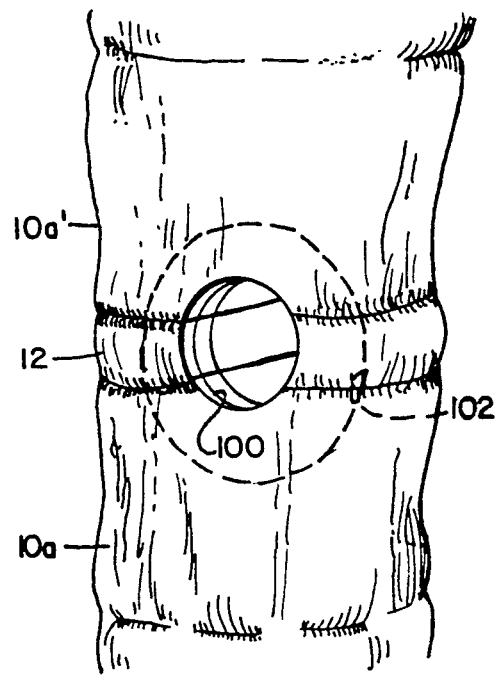
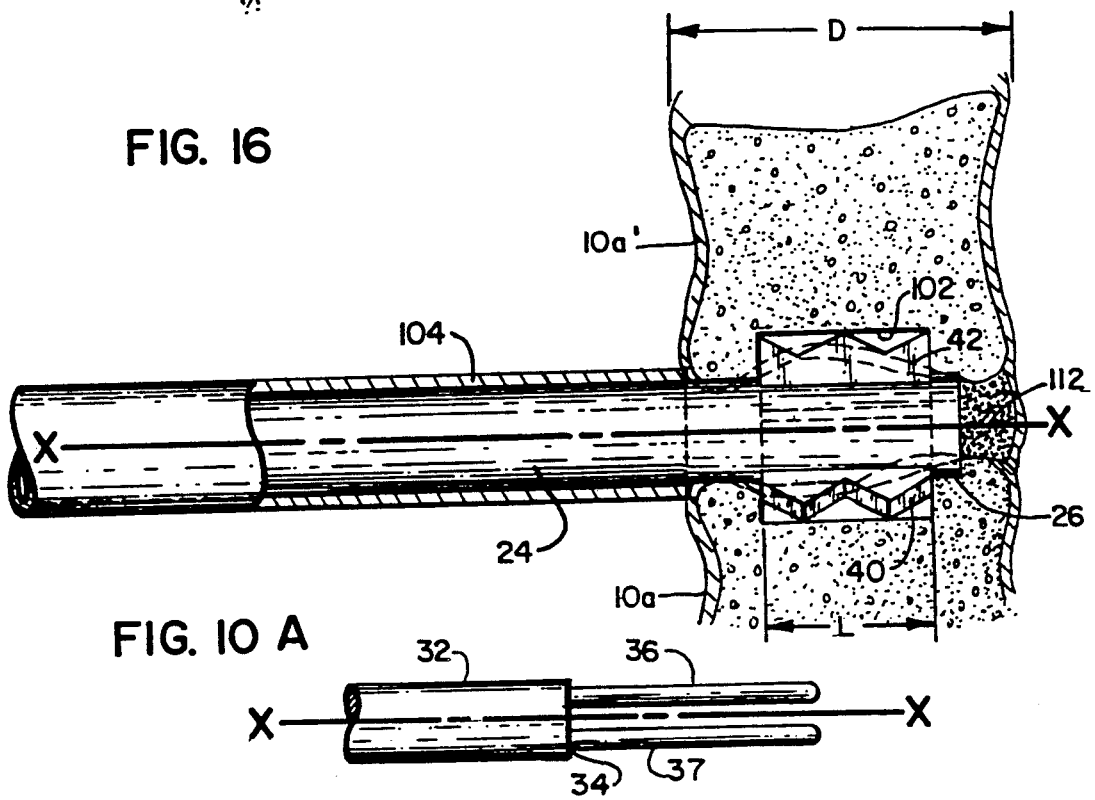

METHOD OF MAKING AN INTERVERTEBRAL REAMER

BACKGROUND OF THE INVENTION

1. Field of the Invention

This invention pertains to surgical procedures for stabilizing a spine. More particularly, this invention pertains to a novel surgical tool for use in such a procedure.

2. Description of the Prior Art

Chronic low back pain is one of the most common and perplexing problems facing the field of orthopedic surgery. In addition to the discomfort of the patient, low back pain has severe adverse societal impacts. Ineffective treatment of low back pain results in increased lost time from work and increased insurance claims. Much more tragic societal consequences arise from the patient's efforts to cope with chronic low back pain. These include loss of income or job, loss of self and family esteem, possible chronic dependence on drugs, alcohol and public relief programs.

In many cases, low back pain can be avoided if relative motion between spinal vertebra can be prevented. Immobilization (or, more commonly, intervertebral stabilization) is sought in a wide variety of treatment methods. To abate low back pain, stabilization is directed to stabilizing contiguous vertebra in the lumbar region of the spine.

While the following list is not exhaustive, it illustrates prior stabilization techniques:

1. Non-Surgical Stabilization

The simplest stabilization is accomplished through use of back braces. The brace is worn externally by the patient to restrict lumbar movement. Unfortunately, the brace is bulky and uncomfortable and limited in its effectiveness.

2. Surgical Stabilization a. Generally

Low back pain is presently believed to be associated with anatomic changes in the discs which separate the lumbar vertebra. Surgical stabilization first identifies the degenerated disc and seeks to rigidly join the lumbar vertebra which are separated by the degenerated disc. Ideally, the surgery effectively replaces the vertebra-disc-vertebra combination with a single rigid vertebra. Various surgical techniques have developed which attempt to approach or approximate this ideal.

b. Anterior Spinal Interbody Fusion

The anterior route for fusion involves a surgeon seeking access to the spine through the front (i.e. stomach area) of the patient. Exposure of major organs and blood vessels is required. Accordingly, due to difficulty and danger, this method has not received wide-spread acceptance.

c. Posterior Interbody Fusion and Postero-Lateral Fusion

Posterior fusion means access to the spine is achieved through the back of the patient. Postero-lateral fusion is similar with access coming more from either or both sides of the patient. Several posterior or postero-lateral techniques are known.

i. Usual Single Level Postero-Lateral Fusion

The usual inter-transverse process fusion involves bone grafts connecting the transverse processes of contiguous vertebra. The transverse processes are bone portions extending radially away from opposite sides of the vertebra body. The grafted bone is commonly taken from the iliac crest.

The inter-transverse process fusion has several drawbacks. Gross destruction of normal anatomy is required. Also, a significant incision is necessary to expose a sufficient area of the lumbo-sacral area in order to perform the surgery. This wide exposure results in high blood loss and significant muscle and bone destruction.

An additional drawback of this technique is that the fusion requires a significant time to become solid. For example, fusion may require nine to twelve months. During this period, the spine is rendered less stable than it was before the operation.

A further disadvantage of this technique is that the fusion occurs between the transverse processes which are spaced from the body of the vertebra. Accordingly, complete stability is not achieved.

ii. Dowel-Type Interbody Fusion

A dowel technique for a posterior interbody fusion is known. In the dowel technique, a bore hole is formed through the degenerated disc area. The diameter of the bore is sized so that cutting takes place both into the disc and the opposing surfaces of the vertebra body. With the bore formed, bone dowels are placed within the bore. If successful, fusion occurs between the bone dowels and the opposing surfaces of the vertebra body.

The dowel-type technique is limited in effectiveness. The size of a bore which can be directly formed into the spine is limited by the access area to the spine. Namely, the vertebra structure, location of the spinal cord, location of important nerves and blood vessels restrict the effective maximum size of the bore which can be formed. As a result of this restriction, the amount of degenerative disc material which can be removed is limited. Also, the surface area of the vertebra body which is exposed and available for grafting is limited.

iii. Grafting Into a Cleaned Interbody Space

This technique requires removal of the degenerate disc. The degenerated disc is removed through chiseling or the like to clean the interbody space. When the interbody spaced is exposed, large bone segments are placed into the space and grafted to the opposing vertebra. This technique has enjoyed a high percentage of successful interbody fusions. However, the procedure is very difficult to perform requiring three to six hours by experienced surgeons. Also, the process of removing the disc exposes major nerves and blood vessels to damage. Due to the danger associated with this technique, it is in limited use.

iv. Need for Improved Techniques

As noted above, there are many techniques for stabilizing vertebra. However, these techniques have individual drawbacks. Due to the extreme economic and sociological impact of chronic low back pain, a need for improved techniques with high effectiveness and decreased risks has long persisted and been sought in orthopedic surgery. However, techniques which meet the dual goal of high fusion with low acceptable risks have evaded the art.

SUMMARY OF THE INVENTION

According to a preferred embodiment of the present invention, a surgical tool is provided for preparing a graft site between opposing vertebra. The tool has a distal end with external dimensions sized to be passed through the patient's anatomy to a point of entry on the spine. Retractable cutting blades are provided on the cutting end. At the discretion of the surgeon, the blades can be extended beyond the predetermined external dimensions to cut a cavity greater than the predetermined external dimensions.

BRIEF DESCRIPTION OF THE DRAWINGS

FIG. 10A is a view of an interior end of a central rod of the tool of FIG. 5;

FIG. 16 is a lateral view showing positioning of the tool of the present invention;

FIG. 17 is a sectional view of a bore and chamber shown in perspective in a spine;

FIG. 18 is the view of FIG. 17 without the view being taken in section;

DESCRIPTION OF THE PREFERRED EMBODIMENT

A. The Prior Art

1. Transverse Process Fusion

Before proceeding with the detailed description of the preferred embodiment, a more detailed description of the prior art will be given with reference to the drawings. It is believed such a description will facilitate the reader's understanding of the apparatus and method of the present invention.

Figure 1:
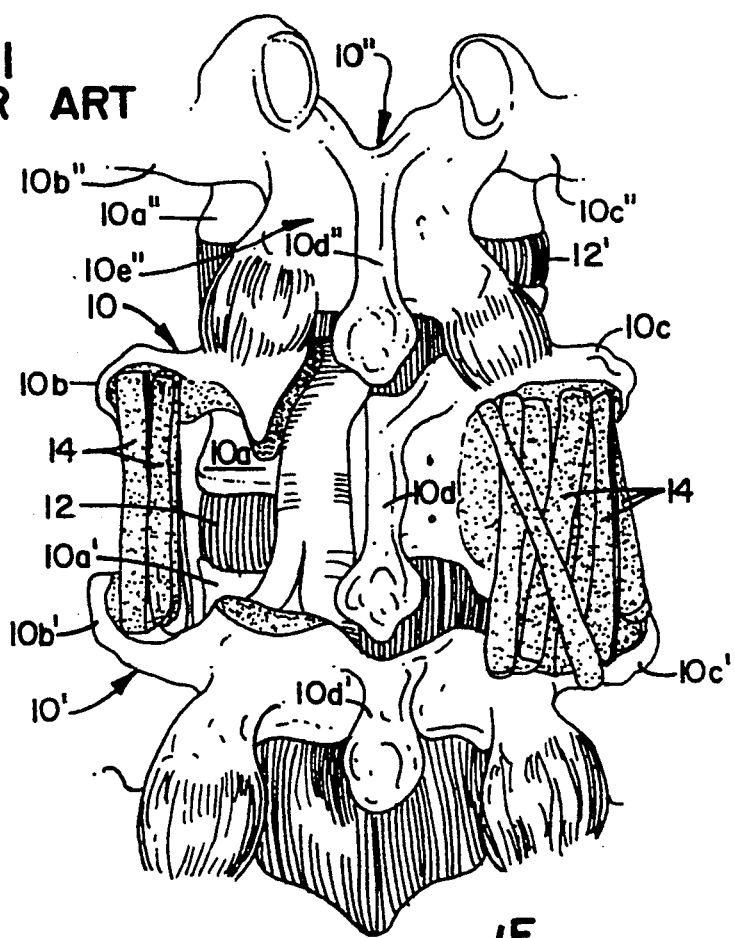
FIG. 1 is a posterior view of a segment of a lumbar spine with a graft made according to the prior art technique.

Referring to FIG. 1, the prior art technique of an intertransverse process fusion is shown. FIG. 1 is a posterior view (i.e., taken through the patient's back) of three lumbar vertebra 10, 10' and 10''. Each of vertebra 10—10'' includes a body portion 10a—10a'' and a pair of laterally projecting bones known as transverse processes 10b—10b'' and 10c—10c''. Also, each vertebra includes a posterior projecting bone known as the spinal process 10d. The vertebra body 10a, 10a' and 10a'' are separated by spinal discs 12 and 12'.

In the view of FIG. 1, disc 12 is a diseased disc which contributes to relative instability between vertebra 10 and 10''. To effect stabilization, bone segments 14 are taken from the iliac crest (not shown) and grafted onto vertebra 10 and 10'' with the grafted bone 14 extending between opposing transverse processes 10c, 10c'' and 10b, 10b''.

In order to perform a transverse process fusion, a surgeon must make an incision in the patient's back and separate tissue and muscle in order to expose the wide area in which the grafting is to take place. This results in gross destruction of normal anatomy as well as high blood loss. Also, this surgical technique does not completely stabilize the vertebra since there is no direct connection between the vertebra body 10a and 10a''.

2. Dowel Interbody Fusion

Figure 2:
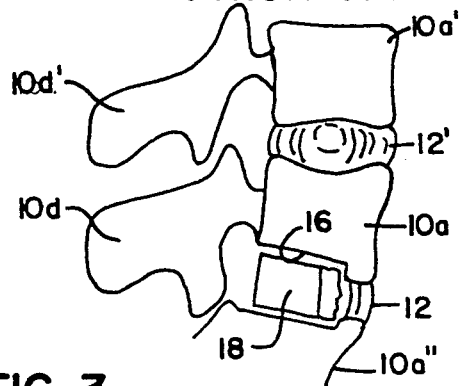
FIG. 2 is a lateral view of a spinal segment showing a prior art fusion technique.
Figure 3:
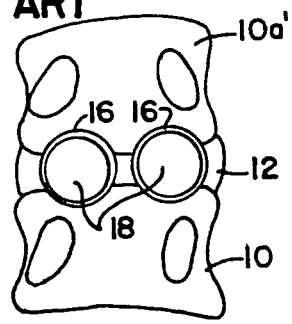
FIG. 3 is a posterior view of the fusion technique of FIG. 2.

The dowel-type interbody fusion referred to previously is shown illustrated in FIGS. 2 and 3. FIG. 2 is a lateral view of the view of FIG. 3. In FIG. 3, only the vertebra body portions 10a, 10a' are shown.

As shown in FIG. 3, two bores 16 are formed into the diseased disc tissue 12. The bores 16 are made as large as possible so that they also cut into the bone of the body portions 10a and 10a''. The bore 16 is formed through either open surgery or percutaneous surgery. In open surgery, the surgeon makes an incision and separates tissue and muscle to expose a wide area of the spine before drilling the bore 16. In the percutaneous method, a small incision is formed and a guide tube is placed against the desired location of tissue 12. The drill bit is based through the guide tube to drill bore 16.

Bone dowels 18 are inserted within the bores 16. In FIGS. 2 and 3, the size of the gap between the bore 16 and the dowel 18 is exaggerated solely for purposes of illustration. In practice, the dowel 18 is made to fit as snugly into the bore 16 as possible.

The technique shown in FIGS. 2 and 3 is limited. The bore 16 is drilled through use of commercially available surgical drill bits. There is a limit on the maximum size of the diameter of bore 16 for any given patient. The limit is attributed to the fact that too large of a drill bit cannot be passed through the patient's body and placed against tissue 12. If too large of a drill bit is used, the size of the bit will interfere and possibly damage other anatomical parts such as important blood vessels, nerves, etc. Due to this restriction only a limited amount of the disease disc tissue 12 is removed. Also, the portion of opposing surfaces of body portions 10a, 10a' which can be removed by the drill bit is limited. This limits the surface area of the graft. This limitation adversely impacts on the potential success of the graft.

3. Grafting In Vacated Intervertebral Space

Figure 4:
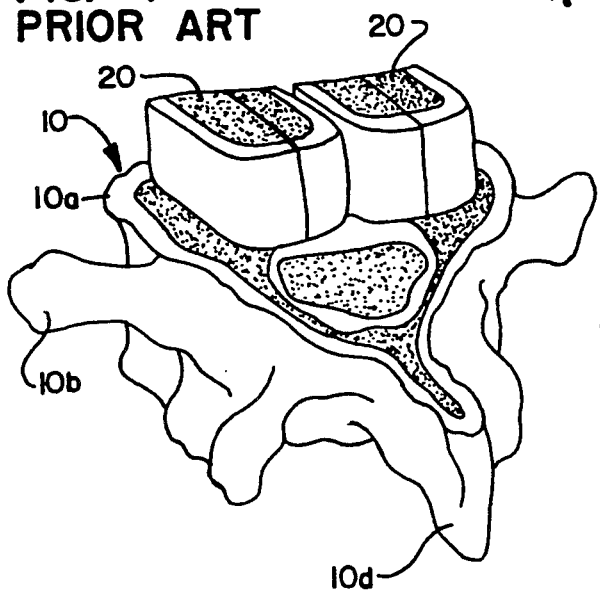
FIG. 4 is a perspective view of a spinal segment showing a prior art fusion technique.

A third prior art method for interbody fusion is shown in FIG. 4. In this method, the surgeon cleans away all tissue between the vertebra to be fused. As a result, all disc tissue 12 as well as disc plates (not shown) are removed. Large surface area bone grafts 20 are placed within the clean space to form a graft between the opposing vertebra bodies.

The technique of FIG. 4 requires fairly complete cleaning of the disc tissue and plates between the vertebra to be fused. This is a time consuming procedure which presents hazard to major nerves and blood vessels in the area of the vertebra. As a result of these risks, this procedure is frequently avoided.

B. Novel Apparatus

1. Main Body

Figure 5:
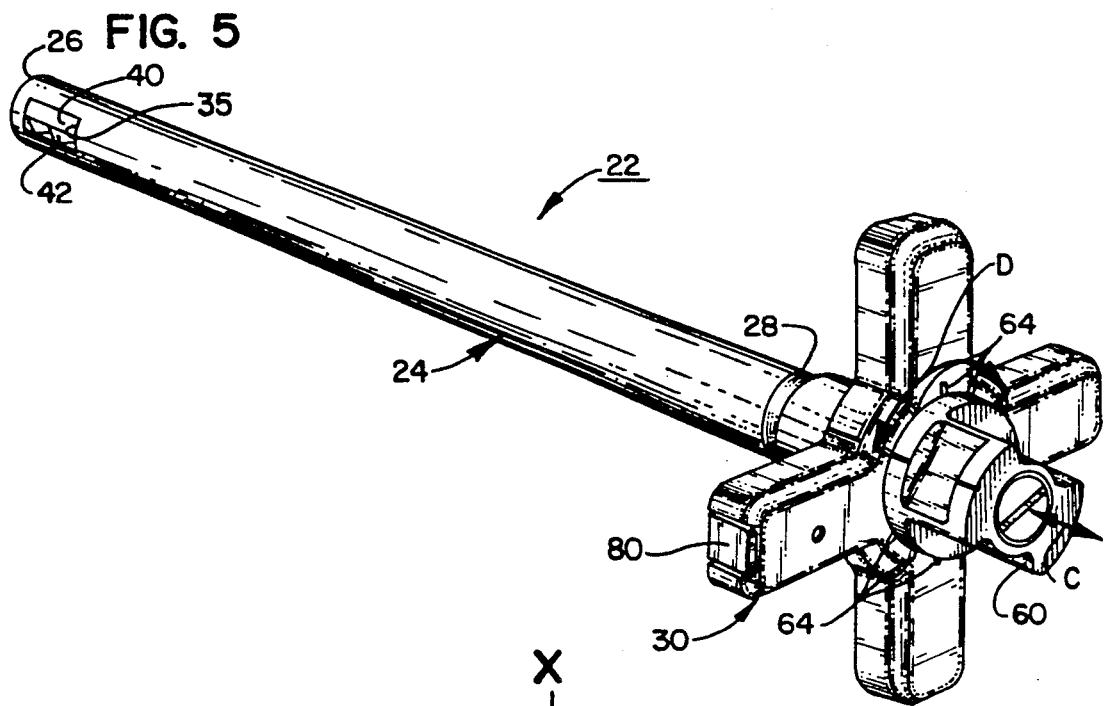
FIG. 5 is a perspective view of a surgical tool according to the present invention.

Reference is now directed to FIGS. 5 through 14 in which identical elements are numbered identically throughout. FIG. 5 is a perspective view of the surgical tool 22 of the present invention. Tool 22 includes an elongate cylindrical shaft 24 having a distal end 26 and an operator engaging end 28. Fixedly connected to the shaft 24 at end 28 is a handle 30. As will be more fully described, the diameter of shaft 24 at distal end 26 is sized such that shaft 24 can be inserted into a patient's body with distal end 26 placed against a diseased disc without shaft 24 having undue interference with other anatomical organs.

Shaft 24 is hollow. As best shown in FIGS. 7-10A, an interior rod 32 is coaxially disposed within shaft 24 and mounted therein for rotational movement about axis X—X. Rod 32 has an exterior end 33 extending axially beyond handle 30. Additionally rod 32 has an interior end 34 (shown in FIGS. 10 and 10A) disposed adjacent distal end 26.

Extending in an axial direction from end 34 are a pair of parallel spaced apart eccentric pins 36, 37 which project off the axial face of end 34 and are spaced from the axis X—X of rotation of rod 32. An end cap 27 covering distal end 26 has an internal annular groove 28 which receives the free ends of pins 36, 37.

2. Cutting Blades

Distal end 26 is provided with a slot 35 extending therethrough. Received within slot 35 are cutting blades 40 and 42 (shown best in FIGS. 11-14). Each of blades 40, 42 is provided with a blade body 41, 43. Bodies 41, 43 are similar in that each have an arcuate first end 44, 46 and an opposite cutting edge 47, 48.

Spaced between arcuate edges 44, 46 and cutting edges 47, 48 are bores 49, 50 extending parallel to edges 44, 46. Bores 49 and 50 are elongated in cross-section and are sized to receive eccentric pins 36, 37. Shown best in FIGS. 12 and 13, the longitudinal cross-sectional dimension of bores 49, 50 extend generally perpendicular to the dimension extending between arcuate edges 44, 46 and cutting edges 47, 48. Shown best in FIG. 12, blades 40, 42 include flat opposing surfaces 51, 52 and opposite flat surfaces 53, 54 which oppose internal flat surfaces 55, 56 of distal end 26.

Blades 40, 42 are sized such that when received in slot 35, blades 40, 42 are slidable relative to one another with surface 51 engaging surface 52 in sliding engagement. Further, surface 53 slidably engages surface 55 and surface 54 slidably engages surface 56.

Figure 11:
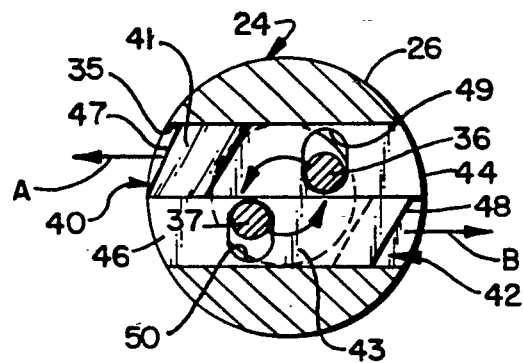
FIG. 11 is a cross-sectional view taken of the tool of FIG. 5 section showing blades disposed within a first position or retracted.
Figure 12:
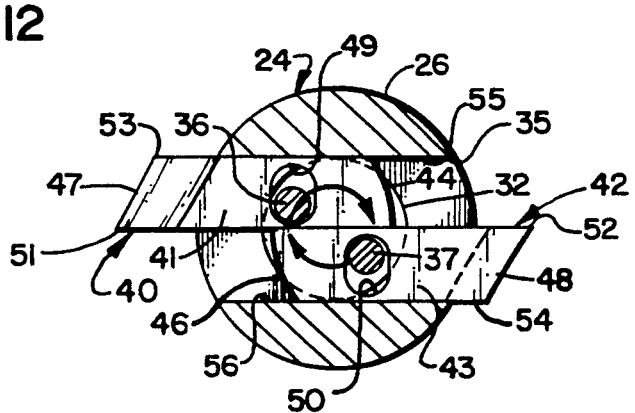
FIG. 12 is the view of FIG. 11 showing the blades in a second or extended position.

The blades are slidable relative to one another between a first, or retracted, position (shown in FIGS. 5 and 11) and a second, or extended, position (shown in FIGS. 12 and 16). When in the retracted position, the blades are completely received within the external dimensions of the distal end 26. Arcuate edges 44, 46 have a radius of curvature the same as that of distal end 26 such that they conform with the external dimensions of distal end 26. Blade edges 47, 48 are completely received within the distal end 26.

When shaft 34 is rotated counterclockwise (when viewed in FIG. 11), pins 36, 37 rotate within bores 49 and 50. The cooperation of the eccentric pins and the bores translates rotational movement of shaft 32 into lateral movement of blade 40, 42 in the direction of the arrows A and B. A 45° rotation of the shaft fully extends the blades to the position shown in FIG. 12. To retract the extended blades, shaft 32 is rotated clockwise (when viewed in FIG. 12).

3. Cutting Blade Control

A control mechanism is provided for controlling the amount of extension of the blades 40, 42 and to hold the blades in a desired extended position. The control mechanism includes an adjustment grip 60 carried on exposed end 33 of rod 32.

Figure 7:
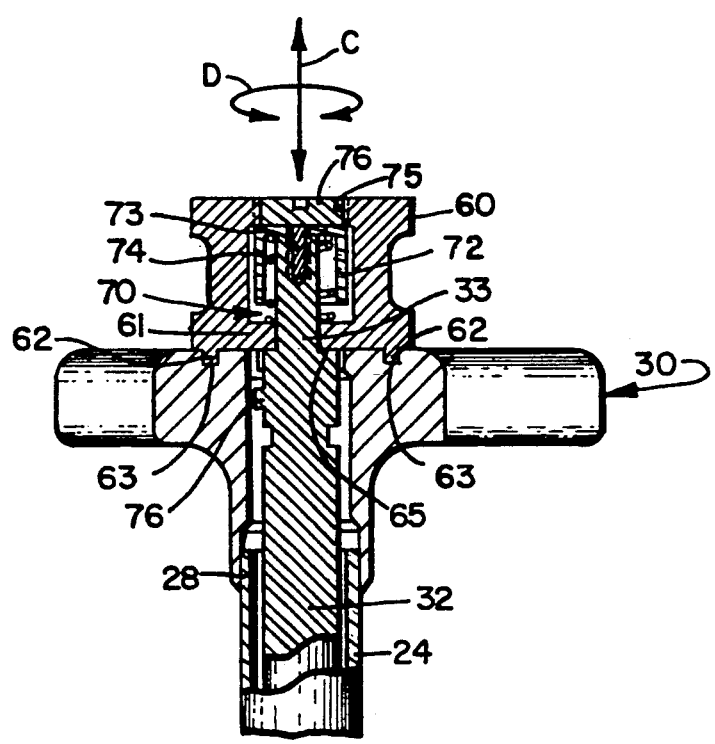
FIG. 7 is the view taken along lines 7—7 of FIG. 6.
Figure 9:
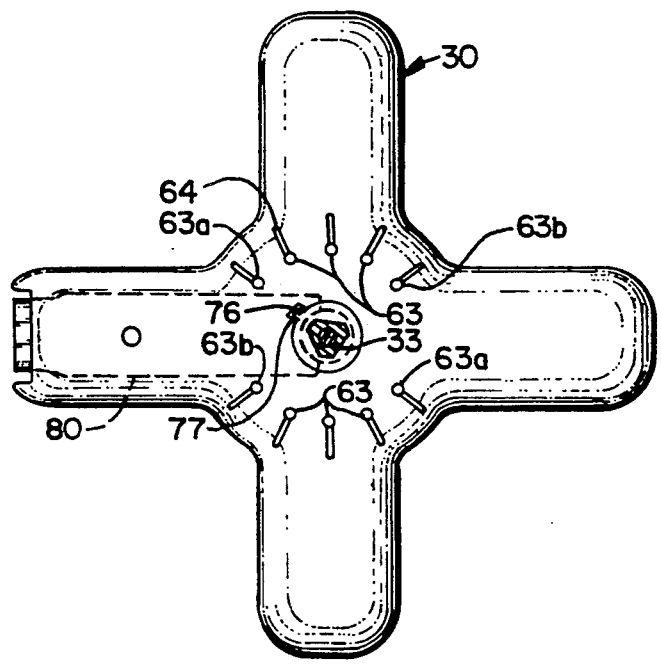
FIG. 9 is the view of FIG. 6 with a control mechanism removed.
Figure 10:
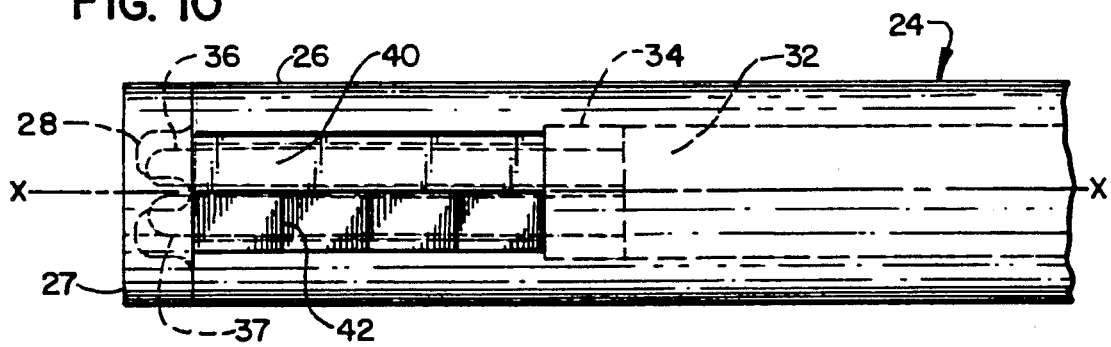
FIG. 10 is an enlarged view of a ristal end of the tool of the present invention.

Shown best in FIG. 7, grip 60 includes a pair of pins 62 opposing handle 30. Pins 62 are sized to be received within any of a plurality of circumferentially spaced holes 63 formed on the surface of handle 30. Holes 63 correspond with positioning of blades 40, 42. For example, with pins 62 received within holes 63a, blades 40, 42 are fully received within distal end 26 as shown in FIG. 11. With pins 62 received within holes 63b, blades 40, 42 are fully extended as shown in FIG. 12. Indicator grooves 64 extend radially away from holes 63 so that a surgeon can sight check the extension of blades 40, 42.

Shaft 32 is rotationally locked to grip 60 by means of free end 33 having a triangular cross-section (best shown in FIG. 9) which is received within a complimentary cross-section opening 65 (see FIGS. 7, 8) of grip 60. Grip 60 may slide axially on free end 33 (in the direction of arrow C in FIG. 7) such that pins 62 may be removed from holes 63 and the handle rotated (in the direction of arrow D in FIG. 7) to any one of a plurality of angularly displaced position with pins 62 reinserted within holes 63.

4. Lock Mechanism

Figure 8:
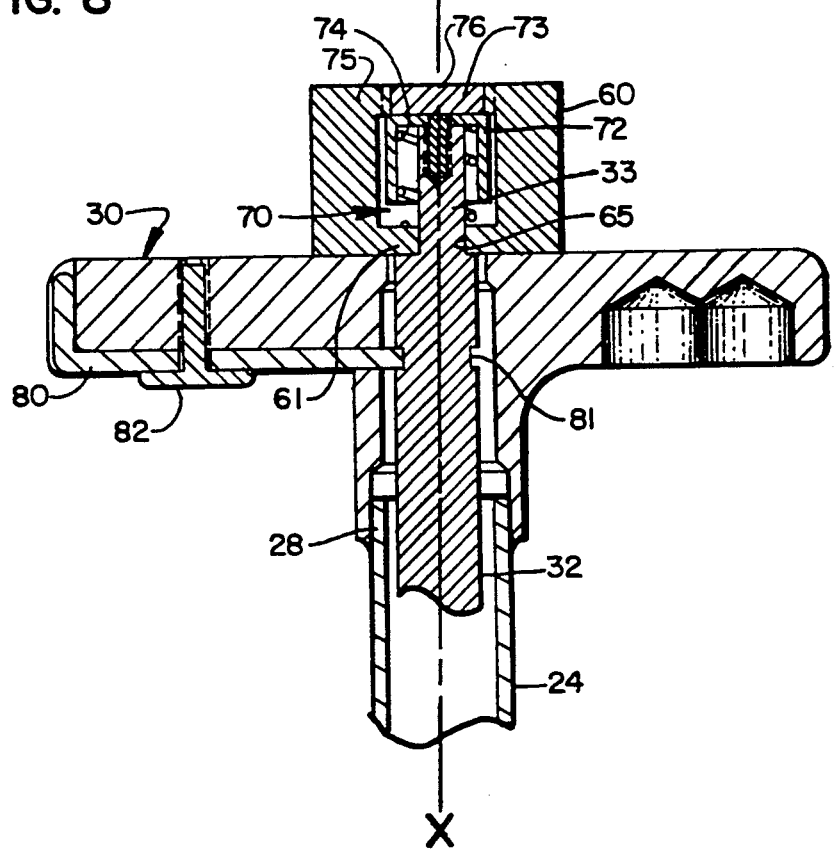
FIG. 8 is the view taken along lines 8—8 of FIG. 6.
Figure 6:
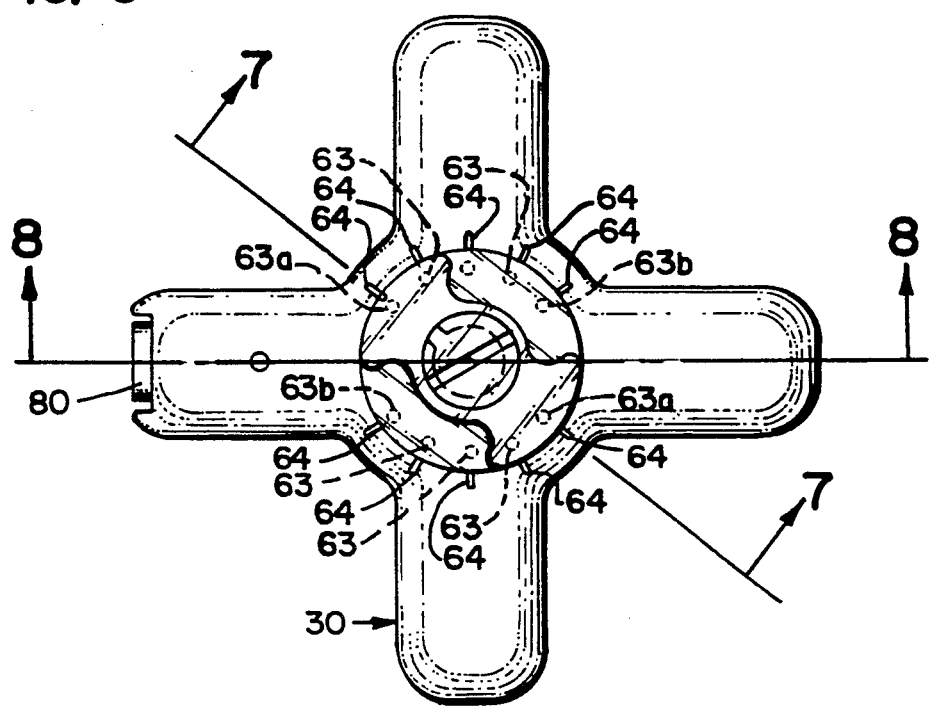
FIG. 6 is a top plan view of the tool of FIG. 5.

Once inserted into desired position, pins 62 are retained within the desired holes 63 by means of a releasable lock structure 70 (shown best in FIGS. 7, 8). The lock structure 70 includes a retaining cup 72 secured to an axial face of free end 33 by means of a screw 73. Cup 72 is spaced from free end 33 with the space sized to accommodate a spring 74. One end of spring 74 abuts cup 70 and the other end of spring 74 abuts an inwardly projecting flange portion 61 of grip 60. Accordingly, grip 60 is urged against handle 30 by means of the urging of spring 74.

To move the pins 62 between other positions, an operator engages grip 60 and forces it in the direction of arrow C against the urging of spring 74 with the operator then rotating both grip 60 and shaft 32 in the direction of arrow D to the desired angular displaced position. The operator releases the grip 60 and the spring 74 urges the pin 62 into the proper hole 63. A threaded hole 75 is formed through the grip 60 to expose screw 73. A threaded cover 76 is provided for closing hole 75.

5. Axial Positioning of Shaft

Shaft 32 can be removed from time to time in order to change or sharpen blades 40, 42. To assemble the apparatus, blades 40, 42 are inserted within slot 35 in the position shown in FIG. 11. To align pins 36, 37 with bores 49, 50, an alignment block 76 (see FIGS. 7, 9) is formed on shaft 32. Alignment block 76 conforms with a hole 77 formed on handle 30. With block 76 and hole 77 aligned, pins 36, 37 are aligned with bores 49, 50. The shaft 32 can then be axially slid into position with the pins received within the bores. To hold shaft 32 in axial alignment, a retaining plate 80 is provided which is sized to be received within an annular groove 81 formed in shaft 32 (best shown in FIG. 8). Alignment plate 80 is held in fixed position by means of a threaded retaining member 82 threadedly received within handle 30.

6. Alternative Cutting Blade Design

Figure 13:
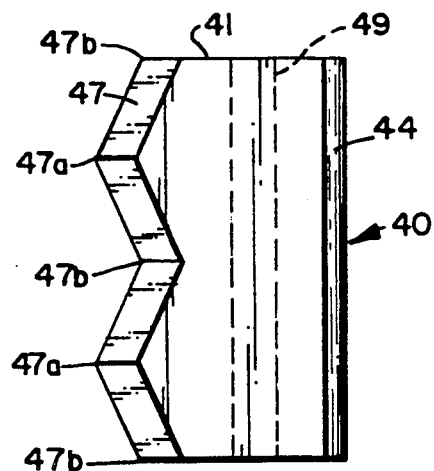
FIG. 13 is a view of a first blade for use in the present invention.
Figure 14:
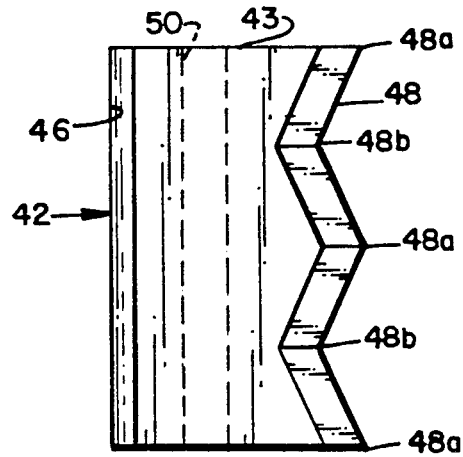
FIG. 14 is a view of a second blade for use in the present invention.

Shown best in FIGS. 13 and 14, blades 40 and 42 are provided with complimentary cutting edges 47, 48. Namely, the peaks 47a of cutting edge 47 are aligned with the troughs 48b of cutting edge 48. Similarly, the peaks 48a of cutting edge 48 are aligned with the troughs 47b of cutting edge 47. As a result, the cooperative cutting action of blade edges 47, 48 form a generally cylindrical hole. It will be appreciated by those skilled in the art that the cutting edges 47, 48 can be adapter such that a wide variety of geometries can be given to a final hole to be cut by the blades. For example, cutting edges 47, 48 could be arcuate (rather than generally linearly) to form a generally spherical hole.

C. Method of Use

To appreciate the novel tool 22, a method of use is now described.

1. Open Method a. Expose Area and Locate Drill Site

The present invention can be used in both open and percutaneous surgical methods. In the open method, the spine is approached from the posterior of the patient using local, spinal or general anesthesia. Using known surgical techniques, the diseased disc and adjacent vertebra are exposed.

b. Drill Access Hole

Figure 15:
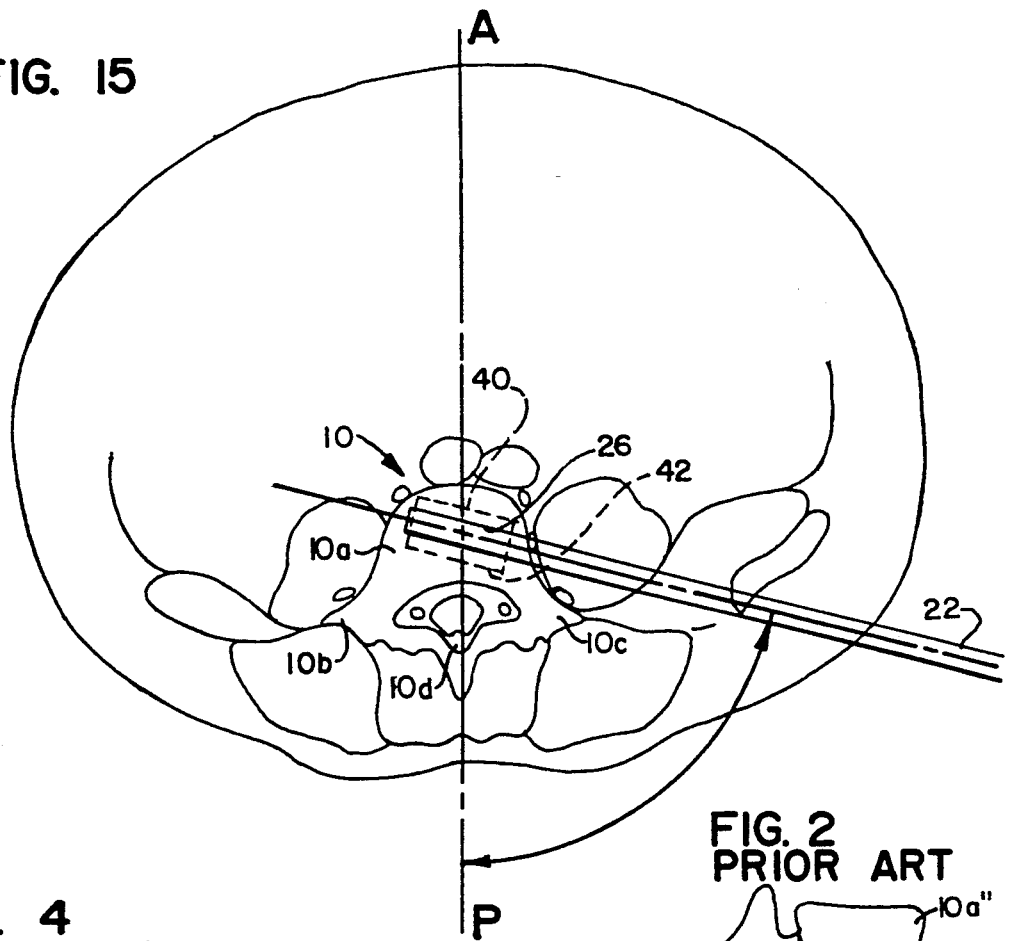
FIG. 15 is a view showing a possible positioning of the tool of the present invention during operation.
Figure 19:
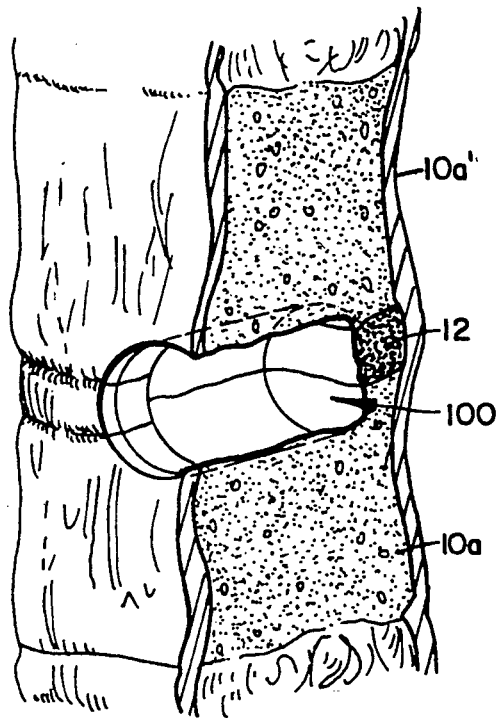
FIG. 19 is a sectional view taken in perspective of an access bore formed in a spine.

With the spine exposed, a bore 100 is formed through the disc layer 12 as shown in FIG. 19. The bore 100 is formed through any conventional means by using a surgical drill bit (not shown). The bit is sized such that the diameter of the bore 100 is approximately the size of the external dimensions of distal end 26 of tool 22 so that distal end 26 may be received within bore 100. The depth of bore 100 is controlled so that distal end 26 can be fully inserted between vertebra body 10a, 10a' (as shown in FIGS. 15 and 16). Controlling depth of a bore hole in a spine is well within the skill of the art.

c. Ream Cavity

With the bore formed, the distal end is inserted within the bore. With distal end 26 completely received within bore, the surgeon incrementally rotates handle 60 to progressively increase the amount of extension of blades 40, 42. At each incremental extension, the surgeon rotates the handle 30 completely about axis X—X so that the blades cut out a large chamber 102 equal to the size of the diameter of the extended blades (see FIGS. 17, 18). After each such cut, the handle 30 is incrementally turned to progressively increase the diameter of the cutting edges of blades 40, 42 until a chamber 102 of desired size (up to the diameter of the fully extended blades 40, 42) is formed. Intermittently, between enlarging the diameter of the enlarged chamber 102, the surgeon may opt to fully retract the blades 40, 42 and remove the tool 22 to flush the chamber 102 being formed. Such flushing techniques are known in the art.

d. Alternative Positioning of Chamber

Figure 20:
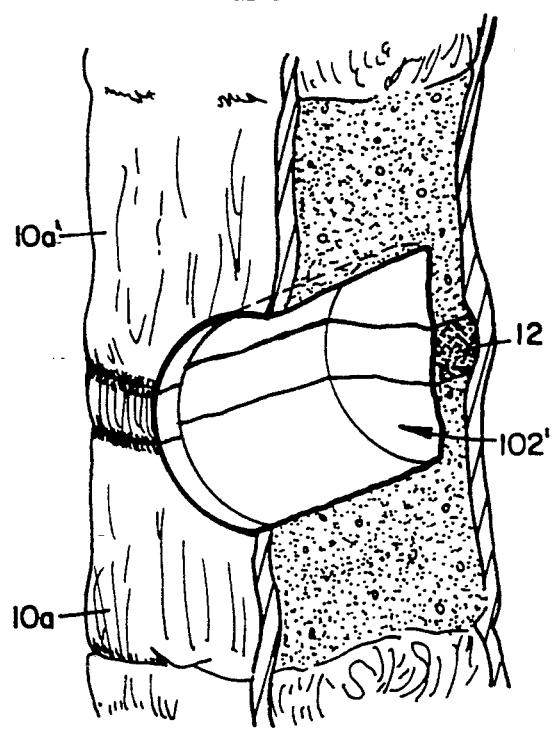
FIG. 20 is the view of FIG. 19 showing the access bore enlarged by a tool of the present invention.

FIGS. 17, 18 shows an enlarged bore fully formed within the interior of opposing vertebra bodies. An alternative is to control the depth of the initial bore 100 such that the enlarged bore 102, is formed flush on the surface of the vertebra bodies as shown in FIG. 20.

e. Filling Chamber with Graft Medium

With the chamber 102 formed and the surgical tool 22 removed, the chamber 102 is filled with any suitable graft medium 103 (see FIG. 21) such as finely chopped cortical or cancellous bone chips. Upon filling the chamber 102 with the graft medium 103, the patient's wound is closed through known surgical techniques.

2. Percutaneous Surgery

In addition to the open method, the method of the present invention with use of the novel tool of the present invention may be used with a percutaneous surgical technique. In the percutaneous method, the patient is placed in a lateral position similar to that used during a chymopapain installation. Local and intravenous anesthesia is used so that the patient can report any symptoms or nerve irritation during the procedure.

a. Locating Drill Site

The patient's skin is prepped and a plastic drape is applied and the skin and soft tissues are infiltrated with a one percent xylocaine. Under bi-plane fluoroscopic control, a smooth guide pin (not shown) (preferably 2.5 millimeters in diameter) is carefully positioned to line up with the diseased disc 12. The guide pin is driven into the disc and a sheath (not shown) is fitted over the guide pin. A locating cylinder 104 (see FIG. 16) is placed over the sheath. A drill bit (not shown) is passed through cylinder 104 and a hole sized to receive the distal end 26 is drilled into the intervertebral space. It will be appreciated that forming a bore by drilling through a locating cylinder as described is known in the art.

b. Forming Enlarged Chamber

With the access bore 100 so formed, the distal end 26 is guided through the cylinder 104 into the bore. FIG. 16 shows shaft 22 being guided by a locating cylinder 104. The tool 22 is used as described in the open surgery method to produce an enlarged chamber 102 within the disc 12 and surrounding bone 10a, 10a'. This chamber 102 is irrigated from time to time by removing the tool 22 and flushing the chamber 102. Extra xylocaine is injected as necessary.

c. Use of Graft Medium

When the tool 22 has been used as desired to form the chamber 102 of desired size, additional procedures may be done at this time depending upon the needs of the patient. For example, if a disc hernia is being treated, the operation may be terminated at this point since the disc has been effectively decompressed. If fusion is desired, the cavity may be filled with finely chopped cortical or cancellous bone chips impacting the chip to provide some mechanical stability. The patient is then closed through any known surgical techniques. The grafting of the bone chips result in a fusion between the vertebra bodies.

d. Alternative Angles of Entry

Figure 21:
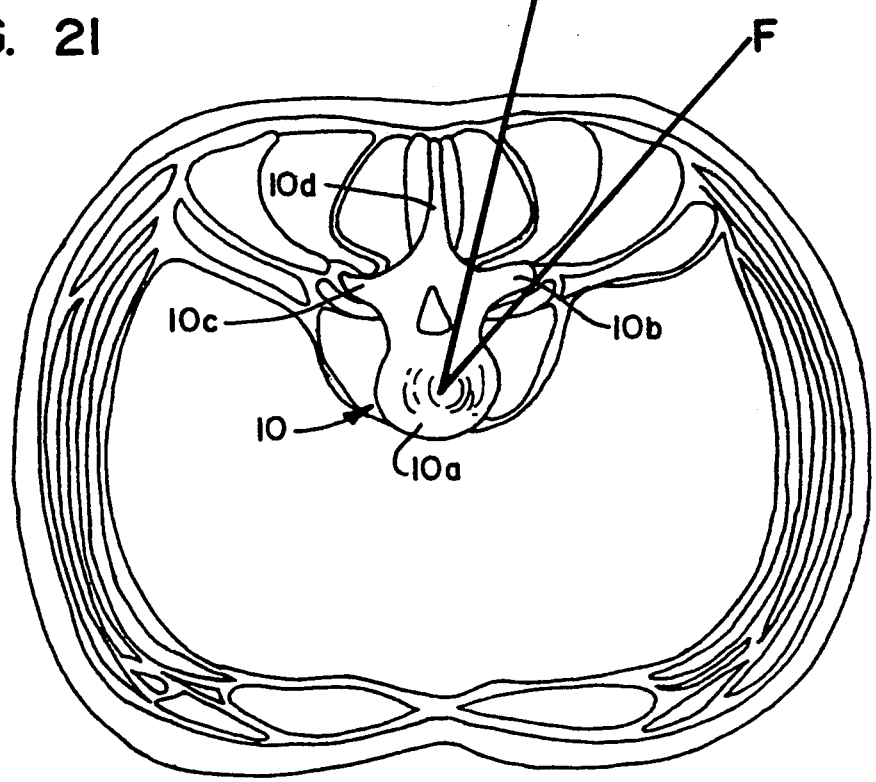
FIG. 21 is a view showing alternate positioning of the tool of the present invention.

FIGS. 15 and 21 show possible angles of entry for the tool when used in the method of the present invention. In FIG. 15, the tool is shown inserted through percutaneous method at an angle of about 75° relative to the anterior-posterior axis, A-P, of the patient. It is believed this angle is suitable for use at the space between the fourth and fifth lumbar vertebra and above. As shown in FIGS. 15 and 16, the distal end 26 is completely received within the vertebra body 10a. FIG. 21 shows alternate angles for insertion of the tool with the size of the tool presenting minimal interference or destruction to other anatomical organs. In FIG. 21, line E shows an angle through the laminar bone. In line F, access is through the soft tissues of the lumbar paravertebral muscles. It is anticipated that the angle E represents a preferred angle for insertion in most situations.

D. Size of Tool

Figure 23:
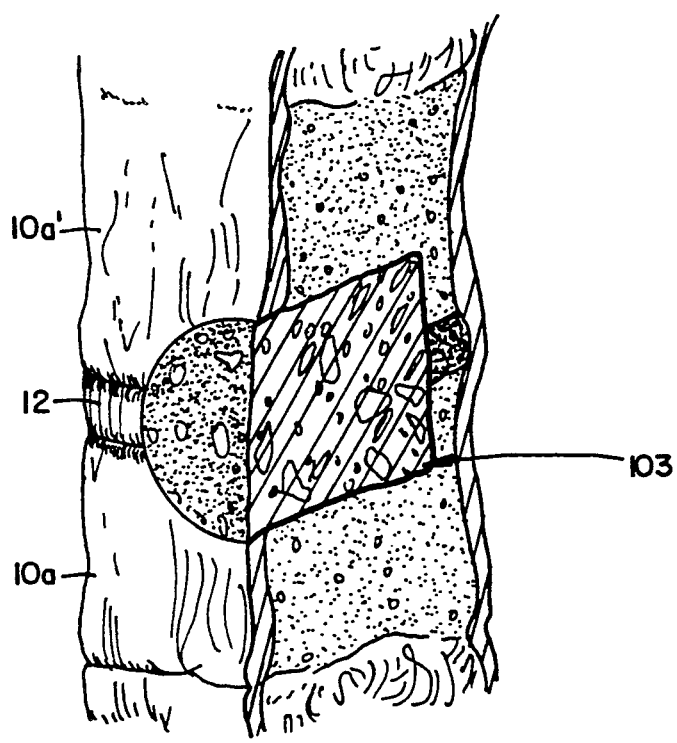
FIG. 23 is the view of FIG. 17 showing a graft medium in the enlarged chamber.

With best reference being made to FIGS. 15, 16 and 23, important dimensions of the tool 22 with respect to spinal anatomy will now be discussed. The dimensions of the distal end 26 and cutting blades 40, 42 are selected with reference to predetermined dimensions of the spine in which the tool 22 is to be used. For example, for use in operating on a human the dimensions are preferably selected with respect to known human vertebra size.

Figure 22:
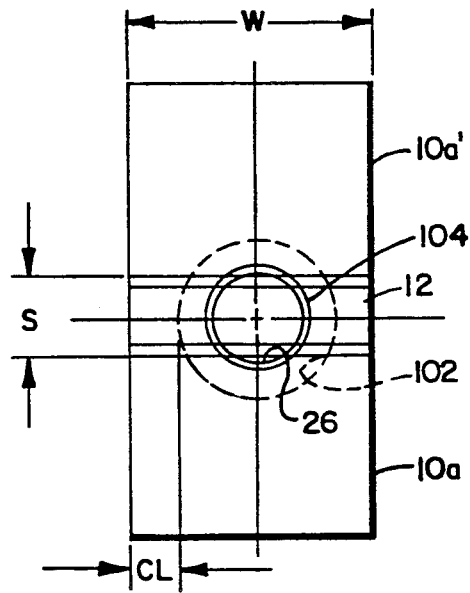
FIG. 22 is a view of a spine showing relative dimensions of spinal elements and a bore made according to the present invention.

Illustrated best in FIG. 22, a typical intervertebral space, S, between the fourth and fifth lumbar vertebra body portions 10a, 10a' is shown. Intervertebral spacing (i.e., the disc height, S) between vertebra is normally 10 millimeters (including disc cartilage and end plates). The width, W, (i.e. the dimension measured between the sides of the vertebra) of the vertebra is about 45 millimeters. The depth, D (see FIG. 16) (i.e., the anterior-posterior dimension of the vertebra) is about 35 millimeters. Such dimensions are typical for an adult human male and may vary with the age and sex of the patient as well as other factors. The dimension will also vary for different locations in the spine.

To avoid interference of the distal end 26 with other anatomical parts and to permit location of the distal end 26 against disc 12, the distal end has a diameter of about 12 millimeters. Accordingly, axis bore 100 (as shown in FIG. 19) is preferably formed with a diameter of about 12 millimeters. A larger access hole would require the drill bit which would unduly interfere with other anatomical parts. The thickness of the locating cylinder 104 results in its diameter being about 15 millimeters (as shown in FIG. 22).

Cutting blades 40, 42 are selected such that in the fully extended position, they cut an enlarged chamber having a diameter of about 22 millimeters. As shown in FIG. 16, the length, L, of the cutting blades (and hence the length of the chamber 102) is shown as 25 millimeters so that the blades can be fully received within the 35 millimeter dimension of the vertebra body depth D (FIG. 16).

When sized as described above, the rotation of the distal end with the extended blades cuts both bone and cartilage (See FIGS. 17, 18, 20, 22). The surface area of the bone is greatly enlarged beyond that which is cut by the prior art boring technique. This greatly enlarged surface area enhances the chances of successful fusion. The diameter of the chamber is held at 22 millimeters so that a clearance, CL, of about 11 millimeters is provided to prevent possible cutting action through the exterior of the spine which could damage important nerves or blood vessels.

The distal end 26 is sized to represent the bore size 100 which could be made with prior art drilling techniques. Namely, this is the size of a rod which can be inserted towards the spine without interference with other anatomical parts. The present tool effectively enlarges the possible bore size through use of the retractable cutting blades. This results in increased amounts of diseased tissue being removed from the disc area and an increase surface area of vertebra bone being exposed for grafting. These dual enhancements cooperate to provide a more effective graft.

The foregoing dimensions and descriptions have been given with respect to human anatomy. It will be appreciated that the present tool and method could be used on any animal spine. However, the dimensions of the tool will vary proportionately with increases or decreases in spinal anatomy between different animal types. Also, in humans, the dimension will vary with numerous factors including anatomic region of the spine, age and sex. For example, the tool and method is not limited to the lumbar region and may be utilized in other regions of the spine where vertebra dimensions may be different than those illustrated. Therefore, several different sizes of the tool 22 is anticipated so a surgeon can select the optimum tool for a given patient.

The size of the tool is selected for the distal end 26 to be as large as possible while avoid undue danger upon insertion. For an anticipated approach, a surgeon may cut away a portion of the laminar portion of the vertebra. The laminar portion is shown in FIG. 1 as item 10e" and is known as the plate-like portion of bone connecting the spinal process 10d" to the facet joints of the spine. For a particular anatomical location, the distal end is sized to permit passage through a partially cut-away laminar of opposing vertebra without need to damage the facet joints. Also, the size restriction of the distal end 26 recognizes that there is a limit to which a surgeon may safely move aside the cauda equina sac.

As previously noted, the enlarged bore can be left vacated for the purposes of decompressing a herniated disc. Alternatively, the chamber can be filled with a graft medium for the purposes of fusing contiguous vertebra. The graft medium described above is bone chips or the like. However, any graft medium (such as a bone dowel or a graft prosthesis) could be used.

From the foregoing, it can be seen how the present invention is attained in a preferred manner. Modifications and equivalents of the disclosed concepts which readily occur to those skilled in the art are intended to be included within the scope of the invention. Thus, the scope of the invention is intended to be limited only by the claims which are, or may hereafter be, appended hereto.

We claim:

1. A method of making a surgical tool for use in spinal stabilization in a mammal spine where said spine has contiguous vertebra, each including a body portion, said body portions being of generally predetermined dimension and spaced apart by a layer of tissue of generally predetermined dimension, said method comprising:
   providing a tool body having an operator engaging end and a distal end;
   sizing said distal end to have external dimensions selected for said distal end to be inserted within an animal body and located against said layer;
   providing cutting means on said distal end for cutting at least a portion of said layer and at least a portion of said body portions to form a chamber within said contiguous vertebra and layer, and with said chamber sized greater than said external dimension; and
   providing control means for controlling a depth of cut of said cutting means between at least a first position with said cutting means retained within said external dimensions and at least a second position with said cutting means extended to form said chamber.

2. A method according to claim 1 wherein said distal end is sized to completely receive said cutting means when said cutting means is in said first position.

3. A method according to claim 1 comprising:
   providing said control means with a grip disposed on said operator engaging end of said body mounted for rotational movement relative to said body,
   connecting said grip to said cutting means to move said cutting means between said first and said second position upon rotation of said grip.

4. A method according to claim 3 further comprising providing said cutting means with at least one blade having a cutting edge disposed generally parallel to an axis of said distal end;
   said cutting edge moveable radially from said axis between said first and second positions;
   said connecting means including means for translating rotational movement of said grip into radial movement of said blade.

5. A method according to claim 4 further comprising providing said connecting means with an eccentric pin connected to said handle and off center of an axis of rotation of said handle;
   said blade including a body portion having pin receiving means for rotatably receiving said eccentric pin;
   whereby eccentric movement of said pin urges said blade between said first and second positions with said pin receiving means accommodating rotation of said pin relative to said blade.

6. A method according to claim 1 further comprising providing said control means with means for locking said cutting means in any one of a plurality of releasably locked positions including said first and second position with said cutting means disposed to cut a chamber of different dimensions at each of said locked positions.

7. A method according to claim 1 wherein said mammal spine is a human spine, said method further comprising sizing said distal end external dimensions for said distal end to be placed against said layer without interference of said tool with anatomical functions.

8. A method according to claim 1 further comprising sizing said cutting means to be received within a spine and chamber without said cutting means extending exterior of said spine.

9. A method for making a surgical tool for use in spinal stabilization in a mammal spine having contiguous vertebra with each including a body portion, said tool comprising:
   providing a tool body having a distal end;
   providing said distal end with a cutting blade moveable between first and second potions, sizing said blade for said blade in said first position to be contained within external dimensions of said distal end, said blade in said second position to be disposed to cut a chamber sized greater than said external dimensions upon rotation of said body means;
   connecting a grip to said body means with said grip rotatable relative thereto about an axis of rotation;
   providing an eccentric pin mounted generally parallel to and spaced from said axis of rotation and disposed for eccentric movement about said axis of rotation upon rotation of said handle, said eccentric pin received within said blade for said eccentric pin to urge said blade to move between said first and second position upon rotation of said grip.

10. A method according to claim 9 wherein said tool body is a hollow shaft; a rod disposed with said shaft coaxial therewith and rotatable relative thereto,
    said eccentric pin carried on an internal end of said rod disposed adjacent said distal end; said grip connected to an opposite end of said rod;
    said blade slidably received within an opening formed in said shaft at said distal end with said blade slidable in a direction radial to an axis of said shaft;
    said blade having a bore disposed to receive said pin.

11. A method according to claim 1 wherein said distal end external dimensions are sized to be received between opposing vertebra through a partially removed laminar without destruction of a faced joint.

12. A method according to claim 9 wherein said distal end external dimensions are sized to be received between opposing vertebra through partially removed laminar without destruction of a facet joint.

* * * * *